United States Patent [19]

Peter Klug

[11] Patent Number: 5,078,707
[45] Date of Patent: Jan. 7, 1992

[54] EXTERNAL URINE COLLECTION DEVICE

[75] Inventor: Kenneth R. Peter Klug, Tucson, Ariz.

[73] Assignee: Sierra Laboratories, Inc., Tucson, Ariz.

[21] Appl. No.: 652,440

[22] Filed: Feb. 8, 1991

[51] Int. Cl.⁵ .................................................. A61F 5/44
[52] U.S. Cl. ...................................... 604/349; 604/346
[58] Field of Search .................................. 604/346–352; 128/842, 844

[56] References Cited

U.S. PATENT DOCUMENTS

| Re. 33,206 | 5/1990 | Conway et al. | 604/349 |
| 3,364,932 | 1/1968 | Beach | 604/352 |
| 3,788,324 | 1/1974 | Lim | 604/352 |
| 4,846,909 | 7/1989 | Klug et al. | 604/352 |
| 4,863,448 | 9/1989 | Berg | 604/352 |
| 4,971,074 | 11/1990 | Hrubetz | 604/349 |

FOREIGN PATENT DOCUMENTS 0008641  6/1900  United Kingdom ................ 604/349

Primary Examiner—David J. Isabella
Assistant Examiner—R. Clarke
Attorney, Agent, or Firm—David G. Rosenbaum

[57] ABSTRACT

A flexible cylindrical sheath arrangement for a male urinary device in which the "press-on" device has a longitudinal opening to accommodate insertion of the male organ. The device is sealed along the length of the male penis by use of adhesive on flaps projecting laterally from the cylindrical sheath. Prior to use, the adhesive is covered with a release lining. The sheath portion is connected to a conical portion which terminates in a tubular urine exhaust passage and communicates urine external to the device.

23 Claims, 1 Drawing Sheet

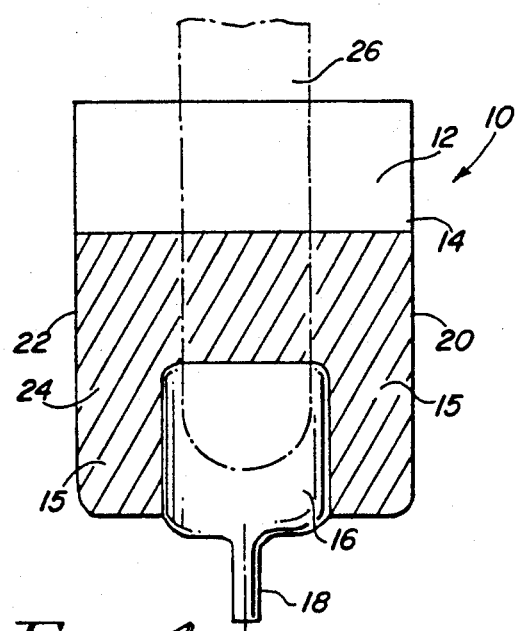 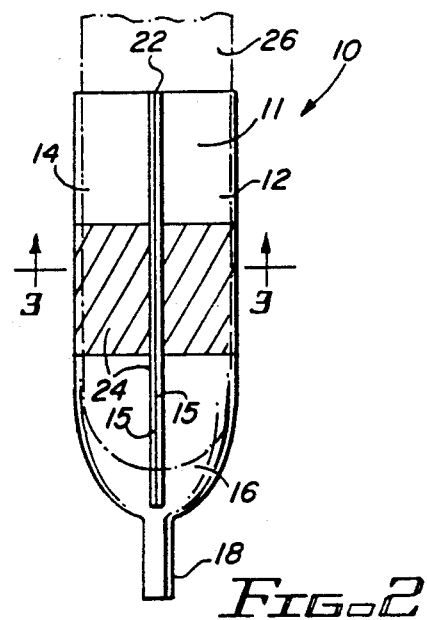 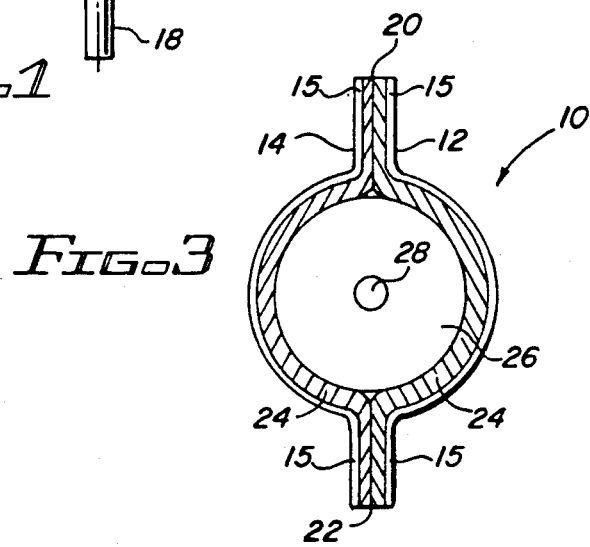 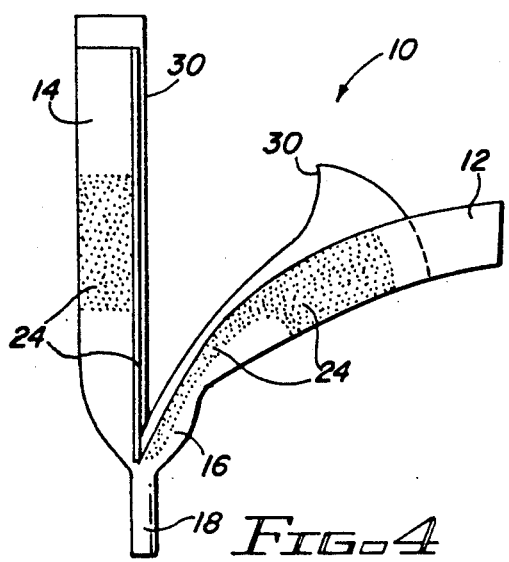 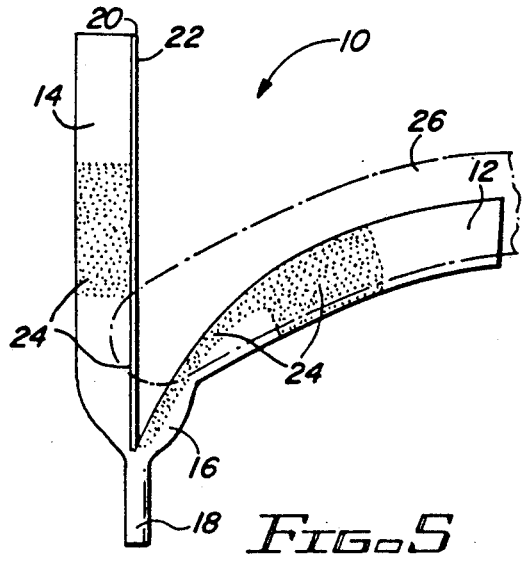

EXTERNAL URINE COLLECTION DEVICE

BACKGROUND OF THE INVENTION

The present invention relates generally to externally applied male urinary catheters. More particularly, the present invention relates to a self-adhesive external male urinary catheter that is easily applied and fits all patients.

Most external male urine collection devices are roll-on condom-like devices. Historically, the first external male catheters were made from condoms with an attached tubular terminus. Improvements in the basic design include reinforcement of the distal end of the catheter, incorporation of a bulb stem to prevent twisting or kinking of the distal end as described in the Klug, et al. U.S. Pat. No. 4,846,909, and the addition of adhesive for ease in application as described in the Conway, et al. U.S. Pat. No. Re.33,206.

Even with these improvements, however, roll-on-type catheters have several limitations.

First, the greatest difficulty is encountered in applying the roll-on-type catheter. The rolled condom catheter is pushed against the head of the penis to unroll the catheter onto the penis. This has the effect of compressing the penis against the abdomen which reduces or eliminates the penile shaft onto which the catheter must be unrolled.

Second, the presence of adhesive on the condom catheter makes application more difficult. Application of a conventional condom catheter requires one hand to grip the penis head and elongate the penis shaft, and the other hand to roll the catheter onto the elongated penis. If the condom catheter is used with adhesive, great manual dexterity is required to apply the double-sided tape or unroll the self-adhesive catheter. Invariably, the care giver's fingers become entrapped in the adhesive, the penis cannot properly be manipulated and, therefore, shortens in length, and since the penis is flaccid, it is extremely awkward to unroll the device.

Third, numerous sizes are required for a proper fit on various sized penises. When a conventional condom catheter is unrolled onto the penis, there is often an unrolled portion left at the base of the penis. This unrolled portion constricts and hinders blood circulation in the penis, and is uncomfortable for the patient during an involuntary erection. It is common practice to cut away the rolled portion that is left after the catheter has been applied. In addition, the condom catheter's diameter will be too small for some patients, causing discomfort, and too large for some patients, leading to fluid leakage from the catheter. Thus, it is improbable for both the length and diameter of the roll-on condom catheter to fit various patients without manufacturing numerous sizes.

Fourth, application of a roll-on condom catheter requires extensive positioning and handling of the male penis by the care giver. Loss of hygiene and disease contagion due to touching the male appendage is a paramount concern to today's care giver. The skin of the penis is often broken; this situation is worsened by repeated application of the roll-on-type catheter. In addition, semen or other body fluids may be present on the penis. Using gloves to minimize risk of disease contagion, makes application of the condom catheter difficult due to the use of adhesive, mentioned previously.

To remedy the difficult of proper fit, U.S. Pat. No. 3,788,324 provided a non-roll-on catheter having a single slit running the length of the condom catheter sheath. However, the device disclosed in this patent does not have overlapping flaps and, therefore, does not realistically deal with the previously listed limitations; preventing backflow of urine, leakage of urine from the slit, and difficulty in application.

SUMMARY OF THE PRESENT INVENTION

The present invention eliminates all the inconveniences described above. The present invention offers a different mode of application in that the conventional condom catheter is a "roll-on" variety, whereas this invention provides a "press-on" device. The collection device is a flexible cylindrical sheath member with an open end and an opposite end which joins a conical portion which terminates in a stem portion. The cylindrical sheath is provided with at least one longitudinal opening in the sheath wall. Side flaps projecting laterally from the cylindrical sheath at the longitudinal opening, adhesively seal to each other, thereby providing a fluid tight engagement along the longitudinal opening.

An adhesive is applied to the inner surfaces of the cylindrical sheath portion and to the inner surfaces of the laterally projecting flaps. The adhesive is backed with a release liner. The adhesive, in conjunction with the laterally projecting flaps, provide a fluid-tight seal along the length of the slit. The adhesive on the inner surface of the cylindrical sheath provides a fluid-tight seal preventing backflow of urine from the open end of the catheter.

Various other objects and features of the invention will be apparent from a consideration of the accompanying specification, claims and drawings.

BRIEF DESCRIPTION OF THE DRAWINGS

FIG. 1 is a side-elevational view of the catheter according to the present invention, showing a penis in phantom.

FIG. 2 is a side elevational view of the flap catheter on a penis, in phantom.

FIG. 3 is a cross-sectional view taken along line 3—3 of FIG. 2.

FIG. 4 is a side elevational view of the catheter of the invention in its opened condition.

FIG. 5 is a side elevational view of the invention illustrating its application to a male member, shown in phantom.

DESCRIPTION OF THE PREFERRED EMBODIMENT

Referring to FIGS. 1 and 2, the flap catheter is indicated by the reference numeral 10. Flap catheter 10 generally comprises a cylindrical sheath member 11 comprising a frontal or anterior portion 12 and a rear or posterior portion 14, which have flap members 15 extending therefrom. Flap members 15 may be integral with or adhesively attached to the frontal and rear portions 12, 14. Frontal portion 12 and rear portion 14 join toward a distal end of the flap catheter 10 to form a conical portion 16. Conical portion 16 terminates in a tubular member 18, which may be connected to an appropriate urine receptacle (not shown) as is well known in the art. The cylindrical and conical portions 11 and 16, respectively, are formed of any thin elastomeric material that is biocompatible with human skin, such as silicone, latex or natural rubber. At least one, but preferably two opposing, longitudinal openings 20, 22, are provided in the wall of the cylindrical sheath 11. It is desirable according to the best mode contemplated for the invention that longitudinal openings 20 and 22 extend the entire length of the cylindrical sheath 11 and terminate in or in close proximity to the conical portion 16, to provide ease of application onto the penis and to accommodate the penis head within the conical portion 16. An adhesive 24 is applied to at least a portion of the inner surface of both the front 12 and back 14 portions, securing the penis 26 in the catheter 10. Adhesive 24 is also provided along longitudinal portions of the flap members 15. Adhesive 24 may be any known biocompatible adhesive which is pressure-sensitive and will provide a fluid tight seal to human skin. As illustrated in FIG. 4, adhesive 24 is preferably backed by a release liner 30, which prevents adhesion between the adhesive 24 coated surfaces during shipping, storage and user application.

As illustrated in FIG. 3, when the flap catheter 10 is applied to the penis, the cylindrical sheath 11 surrounds the circumference of and adhesively engages to the penis. The flap members 15 are adhesively connected in opposing fashion. The flap members 15, in combination with the adherence of the front 12 and back 14 portions to the penis, create a urine/water-tight seal which prevents leakage of urine. This press-on adhesive arrangement also leaves the urethra 28 unconstrained.

FIGS. 4 and 5 illustrate application of the flap catheter 10 to a penis. The longitudinal openings 20, 22 are exposed by retracting the front portion 12 from the rear portion 14 of the cylindrical sheath member 12. The adhesive release liner 30 associated with the front portion 12, or the rear portion 14 is removed, and either the front portion 12 or the rear portion 14 are adhesively engaged upon the penis. The device 10 is positioned on the penis such that the conical portion 16 of the flap catheter 10 engages with the head of the penis as shown. The adhesive 24 of the opposing front portion 12 or rear portion 14 is exposed by removing its release liner 30, and that opposing side of the flap catheter 10 is adhesively engaged upon the penis. The flap members 15 are then adhesively sealed to each other, thereby forming a circumferential adhesion between the cylindrical sheath member 11 and the skin of the penis, and a longitudinal adhesion between opposing flap members 15 associated with each of the front and rear portions 12, 14 of the cylindrical sheath 11. When applied to the penis, the flap catheter 10 is in its assembled condition illustrated in FIG. 2.

An alternative engagement is provided by adhering a first flap member 15 to the penis, e.g., flap member 15 associated with the front portion 12, at a second flap member 15, e.g., flap member 15 associated with the rear portion 14, to the opposing non-adhesive coated side of the first flap member 15 in overlapping or overlying relationship. In this manner, neither of the first nor second flap members 15 protrude laterally from the flap catheter device 10.

It will be seen that the press-on flap catheter application results in an arrangement which is comfortable enough so that it may be worn for long periods of time. Because of the flap members, the flap catheter can be readily applied to any size or shape of penis, thus only one size need be manufactured. The press-on catheter can be easily removed when necessary. While we have shown certain specific embodiments of our invention, it is to be understood that this is only for purposes of illustration and that the scope of the invention is limited solely by the appended claims.

We claim:

1. An external male catheter comprising:
   a cylindrical sheath portion, said cylindrical sheath portion further comprising an anterior and a posterior portion and at least one longitudinal opening therebetween;
   at least one flap member associated with each of said anterior and posterior portions, said at least one flap member projecting from said cylindrical sheath portion in close proximity to said at least one longitudinal opening;
   a conical end portion connected to each of said anterior and posterior portions of said cylindrical sheath member, said conical end portion further comprising a tubular urine exhaust member in fluid flow communication with said conical end portion and said cylindrical sheath member; and
   means for adhesively connecting said anterior and posterior portions to a male organ and each of said at least one flap members to an opposing member.

2. An external catheter as defined in claim 1, wherein each of said cylindrical sheath member, said anterior and posterior portions thereof, said flap members and said conical end portion further comprise elastomeric material.

3. An external catheter as defined in claim 2, wherein said elastomeric material is selected from the group consisting of rubber, latex and silicone.

4. An external catheter as defined in claim 1, wherein said cylindrical sheath portion is characterized by a membranous softness, a stretchability, and a resilience to permit expansion and contraction of the male member.

5. An external catheter as defined in claim 1, wherein each of said anterior and posterior portions of said cylindrical sheath portion form substantially hemispherical aspects of said cylindrical sheath portion.

6. An external catheter as defined in claim 1, wherein each of said at least one flap members associated with each of said anterior and posterior portions of said cylindrical sheath portion further comprise elastomeric strips projecting laterally from said cylindrical sheath portion and extending a substantial lengthwise aspect of and in close proximity to said at least one longitudinal opening.

7. An external catheter as defined in claim 6, wherein each of said elastomeric strips are integrally formed with said cylindrical sheath portion.

8. An external catheter as defined in claim 6, wherein each of said elastomeric strips are operably attached to said cylindrical sheath portion.

9. An external catheter as defined in claim 1, wherein said at least one longitudinal opening extends a substantial lengthwise aspect of said cylindrical sheath portion.

10. An external catheter as defined in claim 8, wherein said at least one longitudinal opening further extends into said conical end portion.

11. An external catheter as defined in claim 1, wherein said means for adhesively connecting further comprises an adhesive selected from the group consisting of rubber, acrylic, hydrocolloid, and foamed plastic.

12. An external catheter as defined in claim 11, wherein said adhesive is applied to an interior surface area of said cylindrical sheath portion and to an interior surface area of each of said at least one flap members.

13. An external male urinary catheter, comprising:
an anterior flap member and a posterior flap member, each of said anterior and posterior flap members having proximal and distal ends thereof, lateral projections extending outwardly from said anterior and said posterior flap members, and comprised of a flexible elastomeric material;
a conical end portion connected to said distal ends of said anterior and poster flap members and having a tubular urine exhaust member in fluid flow communication with said conical end portion; and
means for adhering both of said anterior and posterior flap members to a male organ and interconnecting at least portions of said lateral projections of said anterior and posterior flap members in substantially fluid tight engagement.

14. An external male urinary catheter as defined in claim 13, wherein said elastomeric material is selected from the group consisting of rubber, latex and silicone.

15. An external male urinary catheter as defined in claim 13, wherein each of said anterior and posterior flap members enclosed substantially hemispherical aspects of a male organ when engaged thereupon.

16. An external male urinary catheter as defined in claim 15, wherein each of said anterior and posterior flap members further form laterally projecting, adhesively interconnected, strips when the catheter is engaged upon a male organ.

17. An external male urinary catheter as defined in claim 15, wherein each of said anterior and posterior flap members further form overlaying adhesively interconnected strips when the catheter is engaged upon a male organ.

18. An external male urinary catheter as defined in claim 13, wherein said means for adhesively connecting further comprises an adhesive selected from the group consisting of rubber, acrylic, hydrocolloid, and foamed plastic.

19. An external male urinary catheter as defined in claim 13, wherein said adhesive is applied to an interior surface area of each of said anterior and posterior flap members.

20. A method of applying an external male catheter to the male organ, comprising the steps of:
providing a self-adhering external male urinary catheter having an anterior flap member and a posterior flap member, each of said anterior and posterior flap members having proximal and distal ends thereof and being comprised of a flexible elastomeric material; a conical end portion connected to said distal ends of said anterior and poster flap members and having a tubular urine exhaust member in fluid flow communication with said conical end portion; and adhesive means for adhering both of said anterior and posterior flap members to a male organ and interconnecting portions of said anterior and posterior flap members in substantially fluid tight engagement;
adhesively engaging one of said anterior or posterior flap members upon a surface area of the male organ, such that said anterior or posterior portion forms a first hemispherical aspect covering the male organ, whereby the head of the male organ is disposed within or in close proximity to said conical end portion an in fluid flow communication therewith;
adhesively engaging said second one of said anterior or posterior flap members upon an opposing surface area of the male organ; and
adhesively interconnecting all remaining areas of said anterior and said posterior flap members thereby forming a substantially fluid tight engagement upon the male organ.

21. The method of claim 20, wherein said step of adhesively engaging said second one of said anterior or posterior flap members upon an opposing surface area of the male organ, further comprises the step of adhesively engaging said second one of said anterior or posterior portion to the male organ such that said anterior or posterior portion forms a second hemispherical aspect covering the opposing surface area of the male organ.

22. The method of claim 21, wherein said step of adhesively interconnecting all remaining areas of said anterior and said posterior flap members further comprises the step of interconnecting laterally projecting aspects of each of said anterior and posterior flap members, such that said laterally projecting aspects form an adhesively interconnected, substantially fluid-tight seal along a substantially longitudinal aspect of the male organ.

23. The method of claim 21, wherein said step of adhesively interconnecting all remaining areas of said anterior and said posterior flap members further comprises the step of adhering at least one laterally projecting aspect of each of said anterior and posterior flap members to the male organ, and adhering remaining laterally projecting aspects of each of said anterior and posterior flap members to opposing sides of said adhered at least one laterally projecting aspect in overlapping engagement therewith to form an adhesively interconnected, substantially fluid-tight seal along a substantially longitudinal aspect of the male organ.

* * * * *

UNITED STATES PATENT AND TRADEMARK OFFICE
CERTIFICATE OF CORRECTION

PATENT NO. : 5,078,707
DATED : January 7, 1992
INVENTOR(S) : Kenneth R.P. Klug

It is certified that error appears in the above-indentified patent and that said Letters Patent is hereby corrected as shown below:

ON THE TITLE PAGE

Item [19], "Peter klug" should read --Klug--.

Item [75], "Kenneth R. Peter Klug" should read --Kenneth R.P. Klug--.

Signed and Sealed this

Eighth Day of June, 1993

Attest:

MICHAEL K. KIRK

Attesting Officer     Acting Commissioner of Patents and Trademarks